United States Patent
Jonasson et al.

[19]

[11] Patent Number: 5,937,856
[45] Date of Patent: Aug. 17, 1999

[54] BREATHING DEVICE

[76] Inventors: Hans Jonasson, Rubinvägen 29, S-582 39 Sundsvall, Sweden; Max Jonasson, Biblioteksgangen 4, 2 tr, 183 70 Täby, Sweden

[21] Appl. No.: 08/904,152

[22] Filed: Jul. 31, 1997

[51] Int. Cl.[6] .............................. A62B 7/10; A62B 23/02
[52] U.S. Cl. ................. 128/205.27; 128/200.24; 128/201.13; 128/204.17
[58] Field of Search ................ 128/205.27, 201.13, 128/204.17; 482/13

[56] References Cited

U.S. PATENT DOCUMENTS

| | | | |
|---|---|---|---|
| 3,326,214 | 6/1967 | McCoy | 128/201.13 |
| 4,196,728 | 4/1980 | Granite | 128/201.13 |
| 4,292,966 | 10/1981 | Möno et al. | 128/200.23 |
| 4,478,215 | 10/1984 | Hanlon | 128/201.13 |
| 4,491,130 | 1/1985 | Pasternack | 128/202.26 |
| 4,520,509 | 6/1985 | Ward | 128/206.17 |
| 4,641,644 | 2/1987 | Andersson et al. | 128/200.23 |
| 4,671,268 | 6/1987 | Hunt | 128/201.13 |
| 5,065,745 | 11/1991 | Meier | 128/205.27 |
| 5,438,918 | 8/1995 | Hardester | 128/201.13 |
| 5,590,644 | 1/1997 | Rosenkoetter | 128/201.13 |

*Primary Examiner*—John G. Weiss
*Assistant Examiner*—Joseph F. Weiss, Jr.
*Attorney, Agent, or Firm*—Fasth Law Offices; Rolf Fasth

[57] ABSTRACT

A breathing device that includes a mouth piece that is insertable into the mouth to improve breathing. The mouth piece has an opening defined therethrough to permit exhaling and inhaling of air. A filter holder is attached at a substantially right angle to the mouth piece and has a channel defined therethrough. A removable filter is disposed inside the channel and comprises a corrugated sheet metal that permits condensation of air on the sheet metal when air is exhaled through the mouth piece and into the filter.

17 Claims, 2 Drawing Sheets

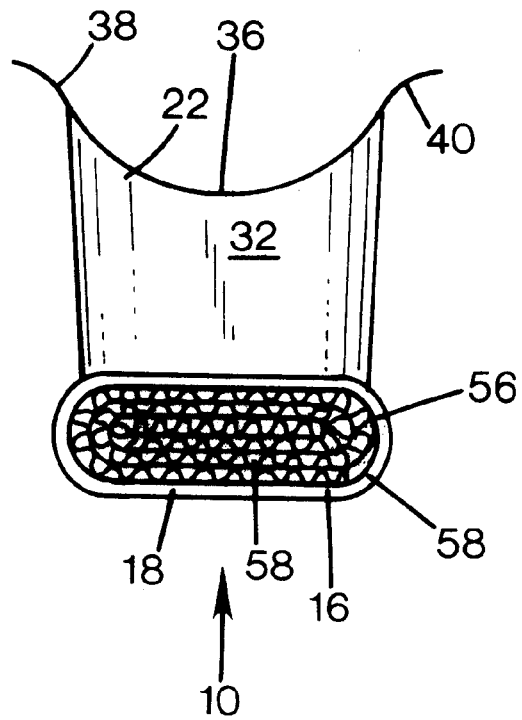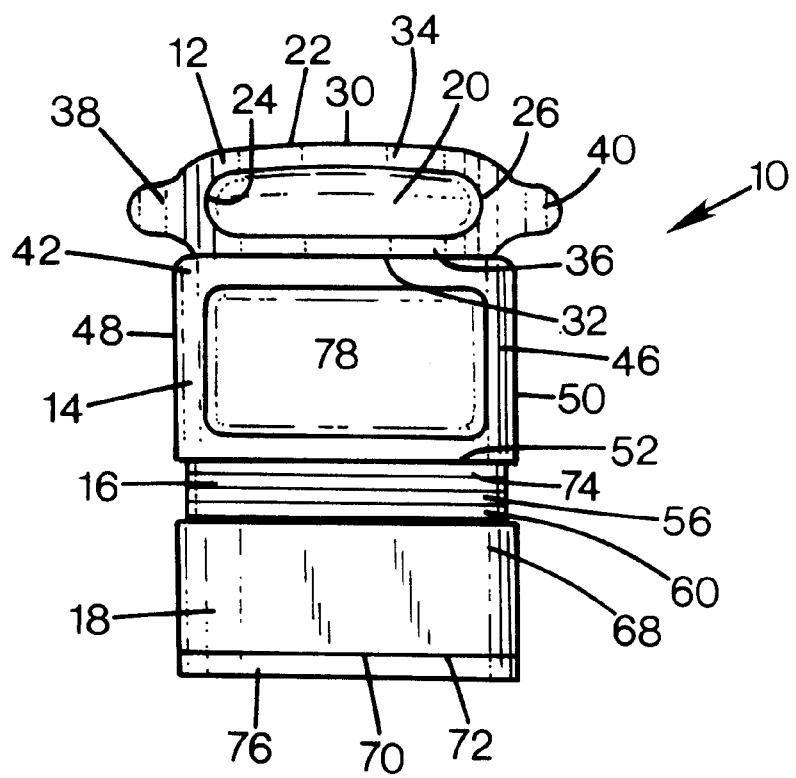

BREATHING DEVICE

TECHNICAL FIELD

The present invention relates to a breathing device that is inserted into the mouth of a person.

BACKGROUND INFORMATION AND SUMMARY OF THE INVENTION

Many people in the very northern and southern hemispheres are suffering from asthma and other breathing problems mainly due to the low humidity in the air combined with low temperatures. The air that we inhale includes a certain amount of water. The amount of water in the air inhaled should be about 44 mg per liter of air to satisfy the water requirement of the lungs. This water concentration is usually obtained at about 37 degrees Celsius at a humidity level of 100%. At 20 degrees Celsius and 50% humidity, the water concentration is 9 mg per liter of air. At 0 degrees Celsius at 50% humidity, the water concentration is only about 3 mg per liter of air. This means that in most climates, the lungs are not getting enough water from the air. It has been shown that this water deprivation is one reason for the development of asthma. As a result, asthma problems are most prevalent in countries with cold climates. There is therefore a need to provide the lungs with sufficient water.

The inhaling of very cold air is another problem that may cause serious and dangerous conditions for the human body. Exposure to very cold air for a long period of time may cool down the body from the inside to a dangerously low temperature and may even cause death. There is a need to be able to increase the temperature of the air inhaled in very cold climates.

Breathing devices that are insertable into the mouth have been developed in the past. Most of them are not very effective and they are uncomfortable to wear. Some of them may even cause damage to the teeth and the mouth.

The breathing device of the present invention provides an efficient method of not only increasing the temperature of the air before it is inhaled into the lungs but the device also increases the humidity of the air inhaled. Additionally, the device is comfortable and safe to wear. The breathing device of the present invention may also be used to prevent the development of asthma.

BRIEF DESCRIPTION OF THE DRAWINGS

FIG. 4 is an elevational bottom view of the breathing device; and

FIG. 5 is an elevational rear view of the breathing device.

DETAILED DESCRIPTION

Figure 1:
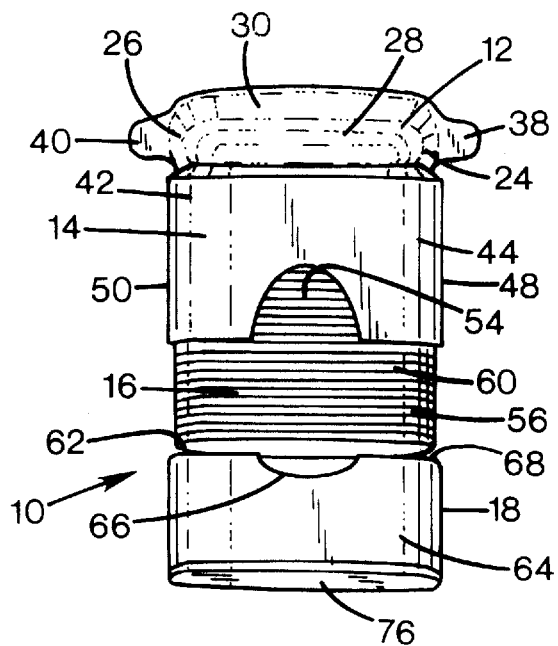
FIG. 1 is a perspective front view of the breathing device of the present invention.
Figure 3:
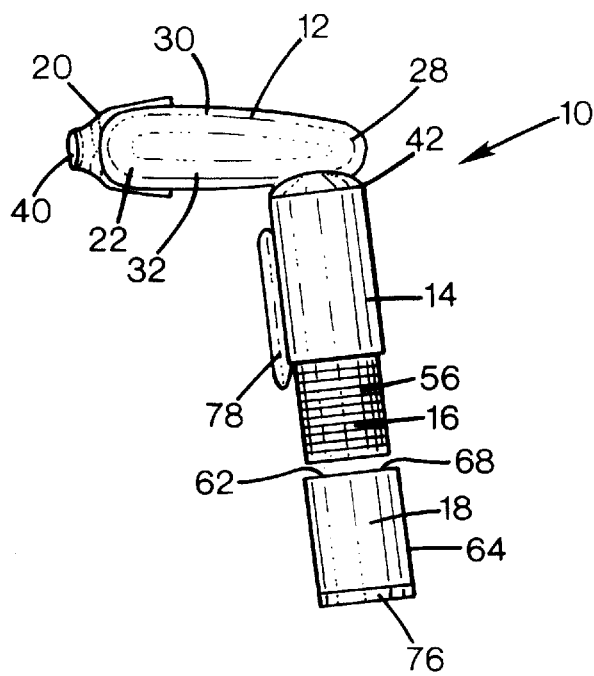
FIG. 3 is a perspective side view of the breathing device.
Figure 2:
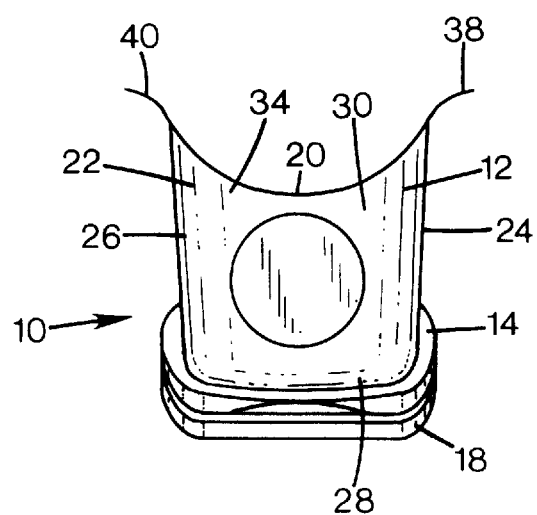
FIG. 2 is a perspective top view of the breathing device.

With reference to FIGS. 1–5, the breathing device 10 of the present invention includes a flat mouth piece 12 attached to a filter holder 14 holding a filter 16 having a filter cover 18 slidably attached to the filter 16. The breathing device 10 may be made of plastic or any other suitable material such as metal and paper.

The mouth piece 12 has an elongate opening 20 defined at an end portion 22 thereof. The opening 20 is defined by curved side walls 24, 26, an end wall 28, a flat upper surface 30 and a flat bottom surface 32. The upper surface 30 and the bottom surface 32 each has thin concave edge portions 34, 36, respectively. A pair of flanges 38, 40 extend outwardly from the concave edge portions 34, 36 so that the flanges extend beyond the side walls 24, 26 and backwardly from the mouth piece 12. In this way, the flanges 38, 40 and the concave edge portions 34, 36 form a smooth concave end portion. The mouth piece 12 is preferably made of a suitable flexible material that does not become stiff or fragile when exposed to cold or warm temperatures. Preferably, the mouth piece 12 is also made of a material that is comfortable to be inserted into the mouth.

An upper portion 42 of the filter holder 14 may be perpendicularly attached to the mouth piece 12 at the end wall 28 of the mouth piece 12. In the preferred embodiment, the angle between the filter holder 14 and the mouth piece 12 is about 100 degrees. It should be understood that other angles may also be used. The filter holder 14 is hollow and has a channel defined therein so that the filter holder 14 is in fluid communication with the mouth piece 12. The filter holder 14 has a flat front surface 44 and a flat back surface 46 that are attached to one another by curved side walls 48, 50. The filter holder 14 has an open bottom portion 52 that is adapted to slidably receive the filter 16 so that the filter may be tightly inserted into the filter holder 14. In this way, the filter 16 is held in place by friction between the filter 16 and the inside of the filter holder 14. The front surface 44 of the filter holder 14 has a semi-circular cavity 54 defined therein at the bottom portion 52. In the preferred embodiment, the filter holder 14 is integral with the mouth piece 12. However, the filter holder 14 may also be separate from the mouth piece 12 so that the filter holder is pivotally attached to the mouth piece 12.

The filter 16 may be flat and elongate and includes a flexible outer skin 56 that may be made of a rubber material or any other suitable material. The outer skin 56 is opened at both outer ends thereof so that a suitable filter material 58. may be enclosed therein. The outer skin 56 has rounded side walls that conform to the curved side walls 48 and 50 of the filter holder 14. The filter material 58 may be a rolled up corrugated metal sheet material that may be slid into the outer skin 56. The sheet material is corrugated to provide a very high surface area, as explained in detail below. The sheet metal has a thickness of about 0.08 mm and may be made of aluminum or any other suitable material. It should be understood that the sheet material may have a thickness ranging from 0.01 mm to several millimeters. At least three different versions of the filter 16 may be used such as sports, energy or classic versions. The classic version is adapted to slow and easy breathing that is typical during walking. Energy is adapted to a slightly more frequent breathing and sports is suitable for strenuous exercising requiring relatively quick and heavy breathing. The sports version provides a breathing resistance that is about 40% less than the breathing resistance, of the classic version. The breathing resistance of the energy version is about 30% less than the classic version. It should be understood that other types of filter may be used. For example, the corrugated metal sheet may be stacked on top of one another.

When the filter 16 is inserted into the filter holder 14, the outer skin 56 is exposed through the cavity 54 of the filter holder 14. The filter 16 has a length that is longer than a length of the filter holder 14 so that when the filter 16 is fully inserted into the filter holder 14, an outer portion 60 sticks out of the filter holder 14.

The filter cover 18 has an opening 62 defined therethrough. The opening is dimensioned to tightly receive the filter 16. The filter cover 18 has a front surface 64 that has a cavity 66 defined therein at an upper portion 68 of the front surface 64. The filter cover 18 has a length that is substantially shorter than the length of the filter 16. When the outer portion 60 is fully inserted into the filter cover 18 so that a bottom portion 70 of the filter 16 is aligned with a bottom end 72 of the filter cover 18, a round or oval cavity is formed by the cavities 54 and 66. In this position, the upper portion 68 of the filter cover 18 abuts the bottom portion 52 of the filter holder 14.

An air cleaning filter 76 may be attached to the bottom portion 70 of the filter 16 or to the bottom portion 52 of the filter cover 18. A wide variety of particle removing filters may be used such as high efficiency particulate air filters. For example, CAMFIL filters manufactured by Camfil Fors. AB, Sweden may be used that removes 95% of particles that are about 0.3 micrometers. More effective filters that remove over 99% of the particles may also be used. The air cleaning filter 76 may have a thickness of about 8–10 millimeters. The filter 76 may also be attached to other parts of the breathing device such as in the mouthpiece 12.

An important feature of the present invention is that the filter holder 14 extends downwardly relative to the mouth piece 12. This reduces the risk of damages to the teeth or jaws if the person falls down or the breathing device 10 is hit by an object because the filter holder 14 rests against the chin. Because the filter holder 14 extends at an angle of between 90–110 degrees relative to the mouth piece 12, the filter holder 14 absorbs some of the impact and it is less likely that the breathing device 10 is pushed into the mouth. The breathing device 10 may replace conventional mouth protection devices commonly used to protect the teeth in sports such as rugby, ice-hockey and American football while providing enhanced breathing. Also, the fact that the filter 16 is separated from the mouth by the length of the mouth piece 12, means that saliva and other objects are likely to remain inside the mouth piece 12 so as not to clog up the filter 16. A clogged up filter 16 is less efficient.

In operation, the mouth piece 12 of the breathing device 10 is inserted into the mouth of a person so that the flanges 38, 40 are comfortably seated in the mouth and the mouth covers the opening 20. In this way, the person is breathing through the breathing device 10 and air may be inhaled and exhaled through the filter 16 containing the corrugate sheet metal having a very high surface area. The breathing device is functioning like a heat exchanger.

When a person is exhaling air through the breathing device 10, the air flows through the mouth piece 12 and out through the filter 16. The humidity in the air exhaled is permitted to condensate on the corrugated sheet metal 58 and the temperature of the sheet metal increases if the outside temperature is below about 35 degrees Celsius (which is the approximate temperature of the exhaled air). The filter 16 is exposed to virtually no saliva because the saliva remains in the mouth and in the mouth piece 12.

When air is inhaled through the filter 16, the temperature of the inhaled air is increased due to the previously heated metal 58 and the humidity of the air is also increased thanks to the condensate on the metal 58. Empirical experiments have shown that an air temperature as low as −35 degrees Celsius is heated up to a temperature exceeding 0 degrees Celsius when the air is inhaled through the filter 16 of the breathing device 10. In this way, the breathing device 10 not only increases the humidity of the air inhaled, the device also increases the temperature of the air before the air enters the lungs. The air cleaning filter 76 cleans the air that is inhaled by removing particles from the air. The removal of particles from the air is particularly important for people with sensitive lungs and other breathing problems such as asthma.

If the breathing device 10 is used in an extremely hot and humid environment, the device may function to reduce the temperature and to reduce the humidity of the air inhaled by permitting the air that is inhaled to condensate on the corrugated metal and be cooled by the metal.

The filter 16 may be replaced by firmly holding the filter 16 in the cavities 54, 66 and pulling the filter 16 out of the filter holder 14. The filter cover 18 is removed from the filter 16 and a new filter is inserted into the filter holder 14 and the filter cover 18 is placed over the filter to protect the new filter.

To accommodate a wide variety of chins and face configurations, the filter holder may be pivotally attached to the mouth piece 12 so that the angle therebetween may be adjusted. A conventional hinge mechanism may be used to connect the filter holder to the mouth piece.

A foam pad 78 may be removably or firmly attached to the flat back surface 46 to provide extra insulation and to make the breathing device 10 more comfortable to wear.

The breathing device 10 of the present invention may be to a helmet or another head piece so that persons that use helmets, such as workers and sportsman. In this way, the breathing device is attached to the helmet and is inserted into the mouth when the helmet is put on the head of the person.

While the present invention has been described in accordance with preferred compositions and embodiments, it is to be understood that certain substitutions and alterations may be made thereto without departing from the spirit and scope of the following claims.

We claim:

1. A breathing device for insertion into a mouth to improve breathing, comprising:

a mouth piece insertable into the mouth and having an opening defined therethrough to permit exhaling and inhaling of air;

a filter holder attached at a substantially right angle to the mouth piece, the filter holder having a channel defined therethrough, the channel being in fluid communication with the opening of the mouth piece, the filter holder having a first length; and a filter slidably disposed inside the channel of the filter holder, the filter comprising a large surface area material to permit condensation of air on the large surface area material when air is exhaled through the mouth piece and into the filter disposed inside the filter holder, the filter having a second length, the second length being longer than the first length so that a portion of the filter protrudes outwardly from the filter holder.

2. The breathing device according to claim 1 wherein the filter is removably attached inside the filter holder.

3. The breathing device according to claim 1 wherein a filter cover is slidably attached to the filter.

4. The breathing device according to claim 1 wherein a foam portion is attached to the filter holder.

5. The breathing device according to claim 1 wherein the mouth piece has outwardly extending flanges attached thereto.

6. The breathing device according to claim 5 wherein the filter is remote from the flanges.

7. The breathing device according to claim 1 wherein the filter is slidably attached to the filter holder and the filter comprises an enclosure having a rolled up corrugated aluminum sheet material disposed therein.

8. The breathing device according to claim 1 wherein the large surface area material is a corrugated sheet metal.

9. A breathing device for insertion into a mouth to improve breathing, comprising:
- a mouth piece insertable into the mouth and having an opening defined therethrough to permit exhaling and inhaling of air;
- a filter holder attached to the mouth piece, the filter holder having a first length and a channel defined therethrough, the channel being in fluid communication with the opening of the mouth piece; and
- a filter slidably disposed inside the channel of the filter holder, the filter having a second length, the second length being longer than the first length so that a portion of the filter protrudes outwardly from the filter holder;
- a filter cover slidably attached to the filter; and
- an air cleaning filter attached to the filter cover.

10. The breathing device according to claim 9 wherein the filter cover defines a first cavity and the filter holder defines a second cavity, the first cavity faces the second cavity so that the filter is exposed at the first and second cavities when the filter is inserted into the filter holder and into the filter cover.

11. The breathing device according to claim 9 wherein the filter holder is substantially perpendicular to the mouth piece.

12. The breathing device according to claim 9 wherein the filter is a corrugated sheet metal having a large surface area.

13. The breathing device according to claim 9 wherein the mouth piece has flanges attached thereto and the filter is remote from the flanges.

14. The breathing device according to claim 9 wherein the filter cover is congruent with the filter holder.

15. The breathing device according to claim 9 wherein the filter is removable from the filter holder.

16. The breathing device according to claim 9 wherein a foam portion is attached to the filter holder.

17. The breathing device according to claim 9 wherein the air cleaning filter is facing away from the opening of the mouth piece.

* * * * *